United States Patent [19]

Porter

[11] Patent Number: 5,429,271
[45] Date of Patent: Jul. 4, 1995

[54] GAME SCENT DISPENSER WITH SCENT WARMER

[76] Inventor: Michael T. Porter, R.R. 1 Box 819 Walloomsac Rd., Bennington, Vt. 05201

[21] Appl. No.: 195,649

[22] Filed: Feb. 14, 1994

[51] Int. Cl.6 .............................. B67D 5/00
[52] U.S. Cl. .............................. 222/3; 43/1; 222/146.5; 222/325; 239/34; 239/136
[58] Field of Search .............. 222/3, 146.2, 146.5, 222/325, 478; 43/1; 239/135, 136, 34, 47

[56] References Cited

U.S. PATENT DOCUMENTS

| | | | |
|---|---|---|---|
| 4,346,059 | 8/1982 | Spector | 239/34 X |
| 4,771,563 | 9/1988 | Easley | 43/1 |
| 4,937,431 | 6/1990 | Jameson et al. | 43/1 X |
| 5,000,383 | 3/1991 | van der Heijden | 239/47 |
| 5,094,025 | 3/1992 | Daniels | 43/1 |
| 5,121,881 | 6/1992 | Lembeck | 239/34 X |
| 5,161,646 | 11/1992 | Aurich et al. | 222/146.5 X |
| 5,305,541 | 4/1994 | Simpson | 43/1 |
| 5,307,584 | 5/1994 | Jarvis | 43/1 |
| 5,359,801 | 11/1994 | Mattucci et al. | 43/1 |

*Primary Examiner*—Andres Kashnikow
*Assistant Examiner*—Joseph A. Kaufman

[57] ABSTRACT

A game scent dispenser that includes a scent warmer to keep the scent aromatic in cold temperature environs.

1 Claim, 2 Drawing Sheets

GAME SCENT DISPENSER WITH SCENT WARMER

BACKGROUND OF THE INVENTION

The present invention generally relates to dispensers for animal scents. More particularly this invention relates to an animal scent dispenser having scent warming means that keep the scent aromatic in cold temperature environs.

Animal scents are widely used by hunters to lure deer and other game to a specific location. Animal scents mask human odors and appeal to the game's sense of smell. Many types of scents are utilized including food scents, territorial infringement scents and sexual attractants. Generally animal scents are liquids sold in small bottles. The hunter disperses the scent in the selected hunting area. The scent is generously applied either to an elevated scent pad disposed in an artificial scrape surrounding an artificial rub (preferably the rub is approximately 24" above ground) and on the artificial rub, or a "scent bomb" is placed on the ground or placed no higher than 24" off the ground. A "scent bomb" is made by pouring the scent into a 35 mm film cannister filled with an elongated strip of clean cotton. The film cannister is capped to tightly seal the scent for transport to the hunting area. At the hunting site cannisters are placed at selected positions upwind of the stand, the cap is removed and with a stick or other elongated object a portion of the scent-soaked strip of cotton is removed from the cannister and draped along the side of the cannister. At the end of a day's hunt the scent-soaked cotton is pushed backed into the film cannister, again using a stick or other elongated object, and the cannister is recapped.

Several problems arise from the above methods of dispersing a game scent. Firstly, filling the cannister with scent and draping the strip of cotton over the side of the cannister to make a "scent bomb" is messy and inconvenient. This operation is particularly difficult in the dark. Also, many of the scents have an odor that is pungent to humans and difficult to remove from skin and clothing, therefore inordinate care in handling is required. Secondly, although the strip of cotton acts as a wick it often dries out very quickly. Thus the scent is rapidly diluted. Thirdly, in cold weather the animal scents tend to freeze and thereby become useless for their purpose. Therefore there is a need in the art for a convenient and hygienic means of dispersing game scents that also keeps the scent from freezing in cold weather.

U.S. Pat. No. 4,953,763 to Kierum et al. discloses a game scent dispenser that includes a scent reservoir having a valved outlet that selectively releases fluid scent to the ground in a drip-like fashion As should be readily understood many of the problems known in the art remain unresolved by the scent dispenser of the Kierum et al. disclosure These and other problems of prior art dispensing of animal scents are overcome by the invention of the present disclosure.

SUMMARY OF THE INVENTION

The game scent dispenser of the present invention generally comprises a housing member having a first vertical compartment and an adjacently-disposed second vertical compartment, the first vertical compartment having an selectively openable top end and a closed bottom end, the second vertical compartment having closed top and bottom ends. A scent warmer is disposed on the floor of the first vertical compartment, a selectively removeable scent reservoir sits on the scent warmer, and a selectively removeable scent dispersing tray is disposed in the upper portion of first vertical compartment above the scent reservoir. A dry cell battery or other power source for the scent warmer is disposed in the second vertical compartment. The game scent dispenser is selectively fastened to a tree or the like by dispenser fastening means attached to an outer wall of the housing member. Preferably, the outer wall of the housing member is camouflaged.

An object of the present invention is to provide a game scent dispenser that eliminates the messy problems associated with making a "scent bomb."

Another object of this invention is to provide a game scent dispenser that keeps the scent concentration at its highest effective level throughout the hunt.

Another object of the present invention is to provide a game scent dispenser with a scent warmer to keep the scent aromatic in cold temperature environs.

A further object of the present invention is to provide a hygienic game scent dispenser.

Another object of the present invention is to provide a game scent dispenser that can be repeatedly used with a variety of animal scents.

It is also an object of this invention to provide a lightweight, easily transportable and low cost game scent dispenser.

These and other objects and advantages of the game scent dispenser of the present invention will be apparent to those skilled in the art from the following description of a preferred embodiment, claims and appended drawings.

DESCRIPTION OF A PREFERRED EMBODIMENT

Figure 1:
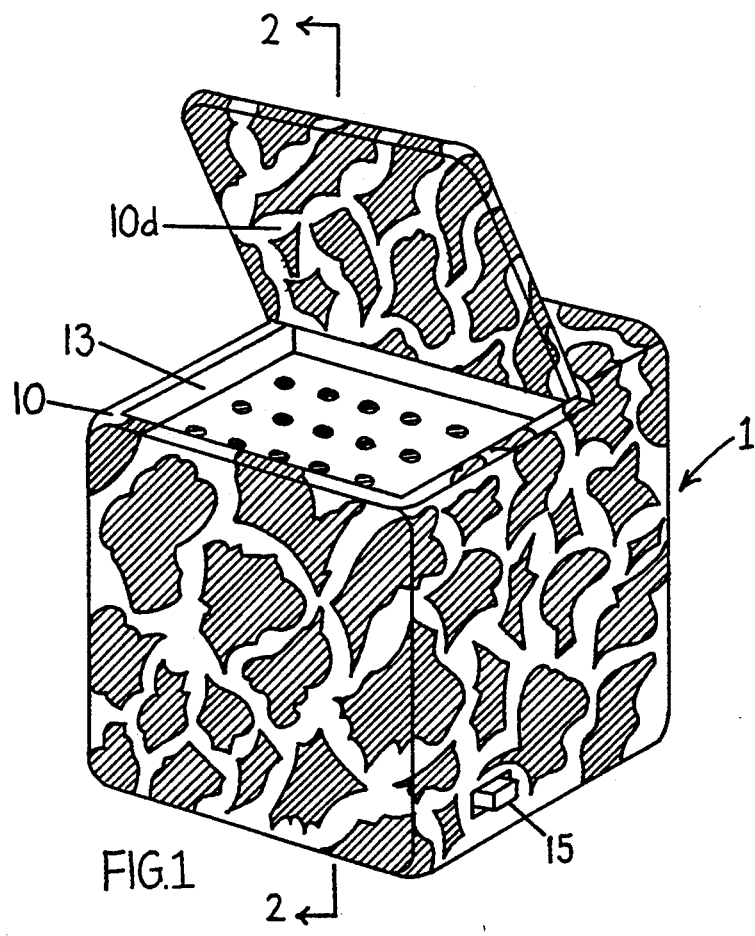
FIG. 1 is a top perspective view of the game scent dispenser of the present invention shown with the housing member lid disposed in a partially open position.
Figure 2:
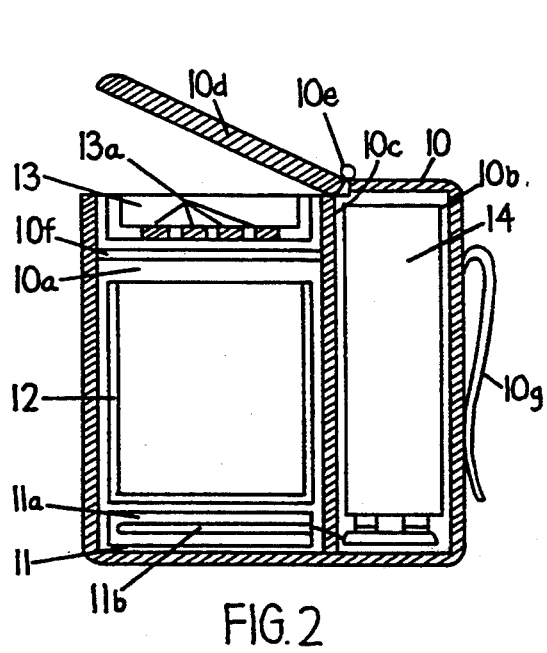
FIG. 2 is a vertical cross-sectional view of the game scent dispenser taken along line 2—2 of FIG. 1.
Figure 3:
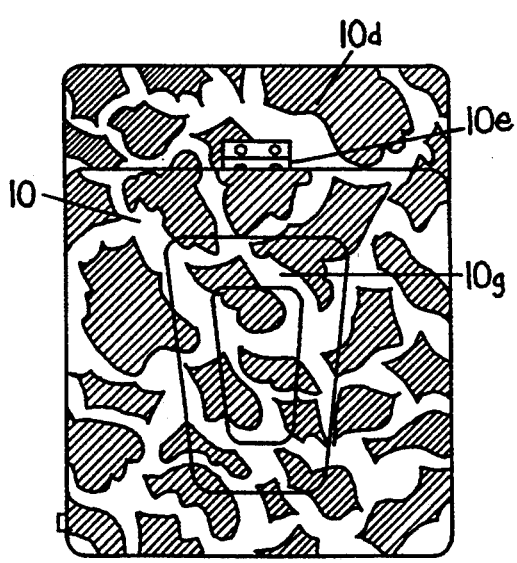
FIG. 3 is a rear elevational view of the game scent dispenser.

FIG. 1 illustrates in a top perspective view the game scent dispenser 1 of the present invention. Scent dispenser 1 generally comprises a substantially hollow housing member 10 having a first vertical compartment 10a and an adjacently disposed second vertical compartment 10b (FIG. 2) formed therein by vertically-extending housing member partition 10c. The exterior of housing member 10 is preferably camouflaged. As can be seen in the vertical cross-sectional view of the scent dispenser 1 illustrated in FIG. 2 the top end of first compartment 10a is open and the bottom end thereof is closed. The top and bottom ends of second compartment are closed. A selectively openable housing member lid 10d is disposed over the top end of first compartment 10a. In the preferred embodiment of scent dispenser 1 housing member lid 10d is pivotally mounted to housing member 10 by meta-stable hinge means 10e. A scent warmer 11 is disposed on the floor of first compartment 10a. Scent warmer 11 preferably comprises a heat conductive block of metal 11a having an electrical coil or other heating element 11b extending through the block of metal 11a. A selectively removeable scent reservoir 12 sits on the top portion of the block of metal 11a. Scent reservoir 12 has an open top end and is provided for receipt of the animal scent used to lure game to the hunting site as hereinafter described in greater detail. A selectively removeable scent dispersing tray 13 is disposed above scent reservoir 12. Scent dispersing tray 13 is seated on a tray seat 10f extending from the interior wall of first compartment 10a. Scent dispersing tray 13 includes a plurality of openings 13a formed in the floor of the tray 13 to baffle the animal scent disposed in scent reservoir 12 and permit the animal scent to disperse to the environs of the animal scent dispenser 1. A dry-cell battery or other power source 14 is disposed in the second vertical compartment 10b and operably connected to the scent warmer 11. A scent warmer switch 15 (FIG. 1) is disposed in a wall of the housing member 10 for selective activation of the scent warmer 11. A dispenser mounting clip 10g is attached to the rear of housing member 10 for selective mounting of scent dispenser 1 to a small tree branch or the like.

For use of the scent dispenser 1 in the field the animal scent is placed into the scent reservoir 12 with the scent reservoir 12 disposed in the first compartment 10a. The scent dispersing tray 13 is then seated on the tray seat 10f. The scent dispenser 1 is then attached to a small sapling or the like by engaging the dispenser mounting clip 10g to the sapling. The housing member lid 10d is then placed in its open position so that the animal scent can disperse to the environs. For cold temperature environs the scent warmer 11 is activated by scent warmer switch 15 to keep the animal scent from freezing and thereby becoming ineffective. Thus, the scent dispenser 1 of the present invention has equal utility in warm or inclimate conditions.

Figure 4:
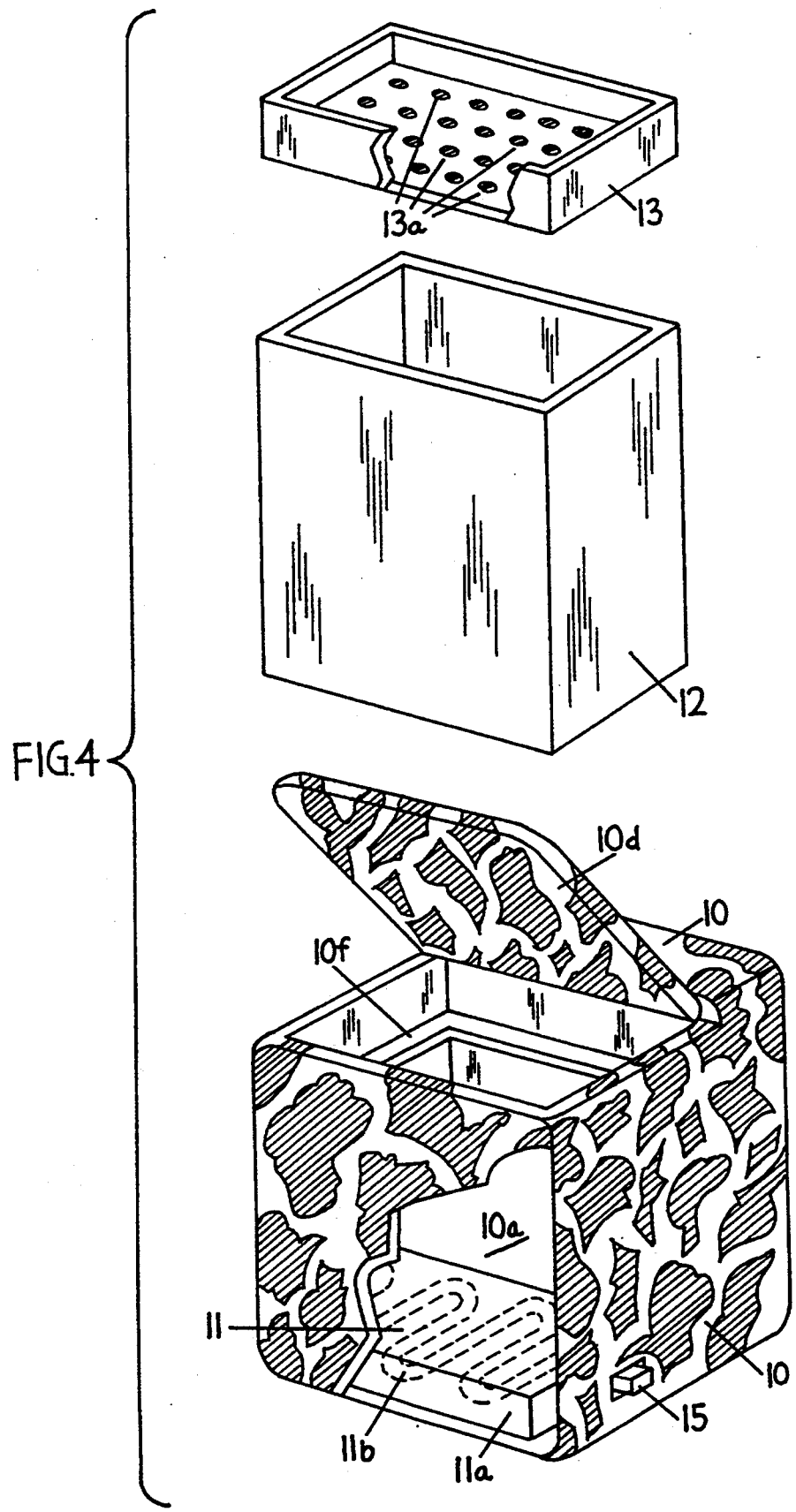
FIG. 4 is an exploded perspective view of the game scent dispenser shown with the housing member lid disposed in a fully open position.

As heretofore described and as shown in the exploded perspective view of the scent dispenser 1 illustrated in FIG. 4, the scent reservoir 12 and the scent dispersing tray 13 can be selectively removed from the first compartment 10a. This permits cleaning of the scent reservoir 12 and the scent dispersing tray 13 if, for example, a different type of animal scent is to be used in the scent dispenser 1. Scent reservoir 12 is preferably sufficiently large to hold an unopened bottle or package of animal scent for secure transport of the animal scent to the hunting site.

Various changes, additions and modifications may be made to the preferred embodiment of the present invention without departing from the spirit and scope of the present disclosure. Such changes, additions and modifications within a fair reading of the appended claims are intended as part of the present invention.

Therefore, in view of the foregoing, I claim:

1. A game scent dispenser comprising a housing member having a first vertical compartment and a second vertical compartment formed by a housing member partition vertically extending through said housing member, said first vertical compartment having an open top end, said housing member including a selectively openable, meta-stable housing member lid disposed above the top end of said first vertical compartment;

a selectively removeable scent reservoir disposed in the first vertical compartment for receipt of an animal scent, said scent reservoir having an open top end;

a selectively removeable scent dispersing tray having a plurality of openings formed in a floor portion of said tray, said scent dispersing tray being disposed adjacent to the open top end of said scent reservoir on a tray seat formed on an inner wall of the first vertical compartment;

a scent warmer disposed in the first compartment adjacent to said scent reservoir;

a scent warmer switch for selective activation of said scent warmer, said scent warmer switch being disposed in an outer portion of said housing member; and scent warmer power means disposed in said second compartment, said power means being remotely operable and operably connected to said scent warmer.

* * * * *